US011158206B2

(12) United States Patent
Vaculin et al.

(10) Patent No.: US 11,158,206 B2
(45) Date of Patent: Oct. 26, 2021

(54) ASSISTING LEARNERS BASED ON ANALYTICS OF IN-SESSION COGNITION

(71) Applicant: International Business Machines Corporation, Armonk, NY (US)

(72) Inventors: Roman Vaculin, Bronxville, NY (US); Rema Ananthanarayanan, New Delhi (IN); Seema Nagar, Bangalore (IN); Kuntal Dey, New Delhi (IN)

(73) Assignee: International Business Machines Corporation, Armonk, NY (US)

( * ) Notice: Subject to any disclaimer, the term of this patent is extended or adjusted under 35 U.S.C. 154(b) by 546 days.

(21) Appl. No.: 16/136,677

(22) Filed: Sep. 20, 2018

(65) Prior Publication Data

US 2020/0098283 A1   Mar. 26, 2020

(51) Int. Cl.
| | |
|---|---|
| *G09B 17/00* | (2006.01) |
| *G06F 3/01* | (2006.01) |
| *G06K 9/00* | (2006.01) |
| *G06F 16/338* | (2019.01) |
| *G06F 40/295* | (2020.01) |

(52) U.S. Cl.
CPC ........... *G09B 17/006* (2013.01); *G06F 3/013* (2013.01); *G06F 16/338* (2019.01); *G06F 40/295* (2020.01); *G06K 9/00302* (2013.01)

(58) Field of Classification Search
CPC combination set(s) only.
See application file for complete search history.

(56) References Cited

U.S. PATENT DOCUMENTS

| | | | |
|---|---|---|---|
| 5,886,683 A | 3/1999 | Tognazzini et al. | |
| 6,305,942 B1 * | 10/2001 | Block | G09B 5/065 |
| | | | 434/156 |
| 8,136,944 B2 | 3/2012 | De Lemos | |
| 8,719,278 B2 | 5/2014 | Karmarkar et al. | |
| 9,230,221 B2 | 1/2016 | Gobert et al. | |
| 9,478,143 B1 * | 10/2016 | Bowen | G09B 5/062 |
| 2003/0038754 A1 | 2/2003 | Goldstein et al. | |

(Continued)

FOREIGN PATENT DOCUMENTS

| | | |
|---|---|---|
| CN | 101567004 | 5/2012 |
| EP | 2600220 | 6/2013 |
| WO | 2016189355 | 12/2016 |

OTHER PUBLICATIONS

Reichle et al., "E-Z Reader: A cognitive-control, serial-attention model of eye-movement behavior during reading," Cognitive Systems Research, vol. 7, Issue 1, Mar. 2006, pp. 4-22.

(Continued)

*Primary Examiner* — Phung-Hoang J Nguyen
(74) *Attorney, Agent, or Firm* — VanLeeuwen & VanLeeuwen; Diana R. Gerhardt

(57) ABSTRACT

An approach is provided that detect a section of a document that is currently being read by a user on a display device as well as the user's current emotional state. In response to determining, based on the detected current emotional state, that reading assistance would be helpful to the user, the approach identifies terminology within the section of the document that is currently being read by the user, retrieves assistive texts related to the identified terminology, and provides the assistive texts to the user at the display screen.

14 Claims, 7 Drawing Sheets

(56) References Cited

U.S. PATENT DOCUMENTS

| | | |
|---|---|---|
| 2009/0097705 A1 | 4/2009 | Thorn |
| 2010/0068683 A1* | 3/2010 | Panec .................... G09B 1/00 |
| | | 434/178 |
| 2016/0259405 A1 | 9/2016 | Wilson et al. |
| 2018/0178372 A1* | 6/2018 | Lee ........................ G10L 15/22 |

OTHER PUBLICATIONS

Anonymous, "System and method to automatically provide optimal content based on vision and eye movement," ip.com, IPCOM000208045D, Jun. 2011, 6 pages.

Sibert et al., "The Reading Assistant: Eye-gaze triggered auditory prompting for reading remediation," UIST '00 Proceedings of the 13th annual ACM symposium on User interface software and technology, San Diego, CA, Nov. 2000, pp. 101-107.

Beckers et al., "Using eye-tracking for the evaluation of interactive information retrieval," I9th International Workshop of the Inititative for the Evaluation of XML Retrieval, INEX2010, Vugh, The Netherlands, Dec. 13-15, 2010, Revised Selected Papers, pp. 185-188.

"Mirametrix," S2 Eye Tracker product sheet, MicroWay Pty Ltd., 1995, 5 pages.

"Software: Cognitive Workload," EyeWorks Software, EyeTracking, Inc., 2011, 4 pages.

Farnsworth, "Eye Tracking: The Complete Pocket Guide," iMotions, Sep. 2017, 50 pages.

"Communicator 5," Tobii Dynavox, product brochure, 2017, 2 pages.

\* cited by examiner

US 11,158,206 B2

ASSISTING LEARNERS BASED ON ANALYTICS OF IN-SESSION COGNITION

BACKGROUND

Assistive technology (AT) can be a powerful way to help learners, such as children or a person new to a language, with reading issues. Traditional reader assistance technology can provide dynamic help to a user during a reading session. However, traditional approaches fail to account for the cognitive ease of reading being performed by the user. In other words, traditional systems provide dynamic help by assuming that the individual reader will find the augmented concept easier to understand without validating the individual's actual understanding of the concept. Further, the known capability of computing cognitive difficulty of a reader reading inside a session is not exploited in traditional systems. Traditional systems provide no rewards in computing an ongoing version that dynamically evolves within a reading session in any way that assists users in understanding unknown concepts. By not understanding an individual's actual knowledge concerning concepts, traditional systems either provide too much information regarding concepts already understood by the reader, and also fail to recognize particular concepts that are unfamiliar to the reader.

BRIEF SUMMARY

An approach is provided that detect a section of a document that is currently being read by a user on a display device as well as the user's current emotional state. In response to determining, based on the detected current emotional state, that reading assistance would be helpful to the user, the approach identifies terminology within the section of the document that is currently being read by the user, retrieves assistive texts related to the identified terminology, and provides the assistive texts to the user at the display screen.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE SEVERAL VIEWS OF THE DRAWINGS

The present invention may be better understood, and its numerous objects, features, and advantages made apparent to those skilled in the art by referencing the accompanying drawings, wherein.

DETAILED DESCRIPTION

Overview of the Invention

Figure 1:
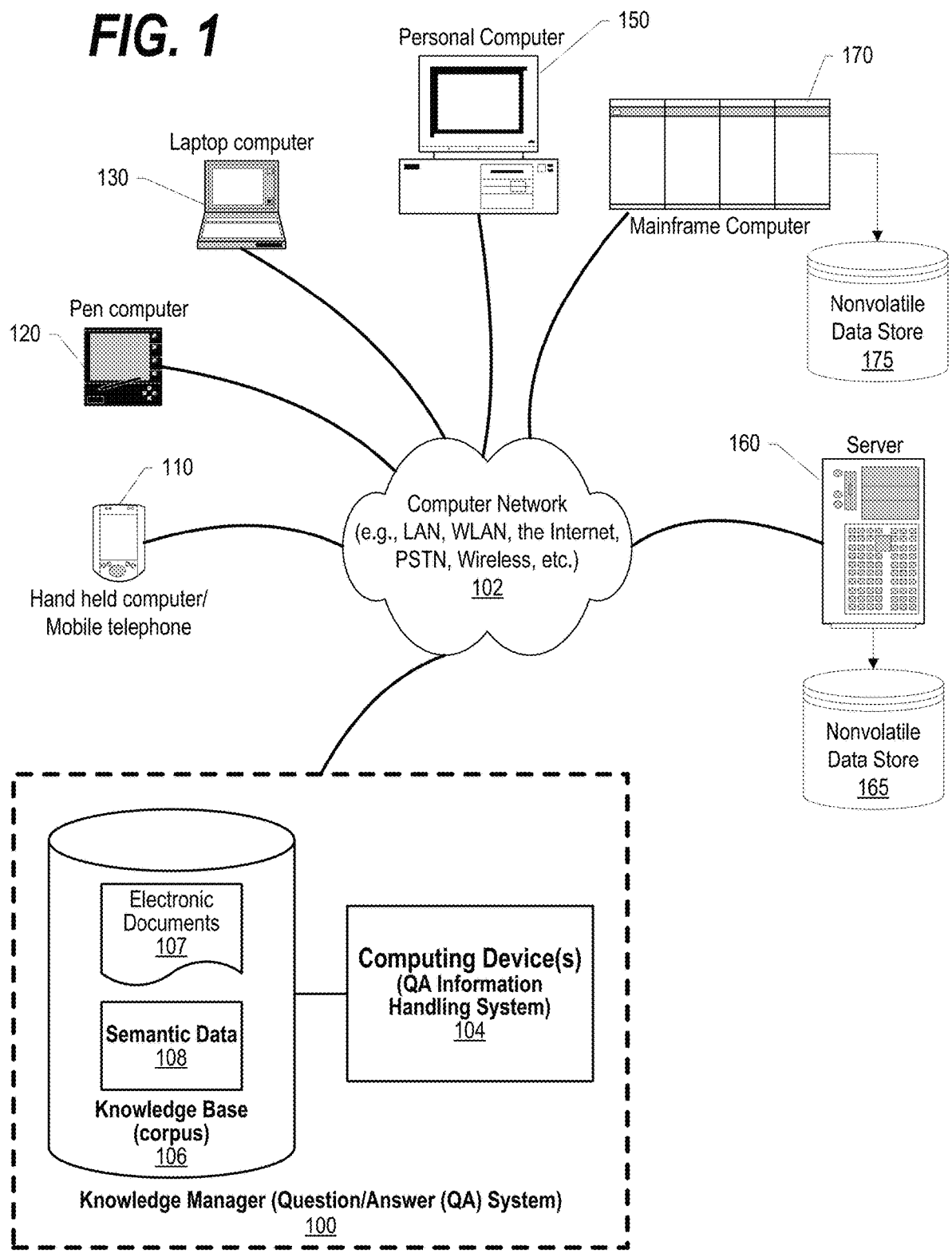
FIG. 1 depicts a schematic diagram of one illustrative embodiment of a question/answer creation (QA) system in a computer network.

FIGS. 1-7 depict an approach that uses eye tracking to identify the portion of a display screen that the user is currently reading, along with the reading rate or reading comfort level being exhibited by the user. Emotion tracking is used to identify the nuances of the user's comfort or discomfort with the reading material, such as the user being, "surprised," "thinking," "upset," "relaxed," etc. during the reading process. Natural Language Processing (NLP) techniques are used to parse the document and link entities based on concepts, keywords, or other factors. When the system detects that the user is encountering difficulty at some part of the document, for instance, by eye tracking the position and emotional tracking the user's current state, then related terms, definitions and concepts from earlier or already—read sections of the same document (or set of documents within the a reading session) may be presented, where the reader's cognition has been found to be smooth, indicating the user's understanding of such other sections. The inference made about the reader's ease of cognition is used to trigger the system which generates context-based help for the user, within the scope of the current document and/or a reading session. The inference is found based upon tracking the user's eye movement and emotional behavior being exhibited.

Interesting features of this approach include the approach being capable of working offline, without connecting to a network (e.g., the Internet, server, backend, LAN, etc.), on an ongoing basis. In addition, the approach provides the ability to provide context-based help to a reader based on inputs generated from tracking the user's eye movement and current emotions. The context used in the approach is with respect to the current document and what has already been read in the document. In this manner, the user receives assistance without having to scroll back and forth, which can be confusing and could cause the user to lose focus and concentration.

Inventive Advantages

The inventors have discovered that a system that assists readers based on analytics of in-session cognition improves the user's interface with the system that is providing the reading material (improved user interface). The system does not necessarily need access to a computer network, such as the Internet, and therefore reduces computing resources used to assist the reader that are otherwise used in conventional approaches. For example, retrieving assistive topics from the Internet might not have the same context as the document being read and might result in traditional approaches providing a poor user interaction and also utilizes additional network resources not needed by this approach, with traditional approaches resulting in wasted computational resources when such network-accessible resources are not needed using the approach provided herein.

While the inventive principles have been described herein with relation to particular types reading material, it will be appreciated that the techniques and methods described herein can be applied to seemingly endless types of material with each of these reading material types being capable of being ingested and processed as described herein to assist the user with cognitive understanding of the material. In addition, the approach described herein does not necessarily require a network connection, however some embodiments may benefit from such a network connection and the approach described herein will also assist users with understanding material accessed over a computer network, such as the Internet.

Terminology and Scope

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. The following detailed description will generally follow the summary of the disclosure, as set forth above, further explaining and expanding the definitions of the various aspects and embodiments of the disclosure as necessary.

FIG. 1 depicts a schematic diagram of one illustrative embodiment of a question/answer (QA) system 100 in a computer network 102. QA system 100 may include knowledge manager 104, which comprises one or more processors and one or more memories, and potentially any other computing device elements generally known in the art including buses, storage devices, communication interfaces, and the like. Computer network 102 may include other computing devices in communication with each other and with other devices or components via one or more wired and/or wireless data communication links, where each communication link may comprise one or more of wires, routers, switches, transmitters, receivers, or the like. QA system 100 and network 102 may enable question/answer (QA) generation functionality for one or more content users. Other embodiments may include QA system 100 interacting with components, systems, sub-systems, and/or devices other than those depicted herein.

QA system 100 may receive inputs from various sources. For example, QA system 100 may receive input from the network 102, a corpus of electronic documents 107 or other data, semantic data 108, and other possible sources of input. In one embodiment, some or all of the inputs to QA system 100 route through the network 102 and stored in knowledge base 106. The various computing devices on the network 102 may include access points for content creators and content users. Some of the computing devices may include devices for a database storing the corpus of data. The network 102 may include local network connections and remote connections in various embodiments, such that QA system 100 may operate in environments of any size, including local and global, e.g., the Internet. Additionally, QA system 100 serves as a front-end system that can make available a variety of knowledge extracted from or represented in documents, network-accessible sources and/or structured data sources. In this manner, some processes populate the knowledge manager with the knowledge manager also including input interfaces to receive knowledge requests and respond accordingly.

In one embodiment, a content creator creates content in a document 107 for use as part of a corpus of data with QA system 100. The document 107 may include any file, text, article, or source of data for use in QA system 100. Content users may access QA system 100 via a network connection or an Internet connection to the network 102, and may input questions to QA system 100, which QA system 100 answers according to the content in the corpus of data. As further described below, when a process evaluates a given section of a document for semantic content, the process can use a variety of conventions to query it from knowledge manager 104. One convention is to send a well-formed question.

Semantic data 108 is content based on the relation between signifiers, such as words, phrases, signs, and symbols, and what they stand for, their denotation, or connotation. In other words, semantic data 108 is content that interprets an expression, such as by using Natural Language Processing (NLP). In one embodiment, the process sends well-formed questions (e.g., natural language questions, etc.) to QA system 100 and QA system 100 may interpret the question and provide a response that includes one or more answers to the question. In some embodiments, QA system 100 may provide a response to users in a ranked list of answers.

An example of QA system 100 may be the IBM Watson™ QA system available from International Business Machines Corporation of Armonk, N.Y., which is augmented with the mechanisms of the illustrative embodiments described hereafter. The QA knowledge manager system may receive an input question which it then parses to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question.

The QA system then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA system. The statistical model may then be used to summarize a level of confidence that the QA system has regarding the evidence that the potential response, i.e. candidate answer, is inferred by the question. This process may be repeated for each of the candidate answers until the QA system identifies candidate answers that surface as being significantly stronger than others and thus, generates a final answer, or ranked set of answers, for the input question.

Types of information handling systems that can utilize QA system 100 range from small handheld devices, such as handheld computer/mobile telephone 110 to large mainframe systems, such as mainframe computer 170. Examples of handheld computer 110 include personal digital assistants (PDAs), personal entertainment devices, such as MP3 players, portable televisions, and compact disc players. Other examples of information handling systems include pen, or tablet, computer 120, laptop, or notebook, computer 130, personal computer system 150, and server 160. As shown, the various information handling systems can be networked together using computer network 102. Types of computer network 102 that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. Some of the information handling systems shown in FIG. 1 depicts separate nonvolatile data stores (server 160 utilizes nonvolatile data store 165, and mainframe computer 170 utilizes nonvolatile data store 175). The nonvolatile data store can be a component that is external to the various information handling systems or can be internal to one of the information handling systems. An illustrative example of an information handling system showing an exemplary processor and various components commonly accessed by the processor is shown in FIG. 2.

Figure 2:
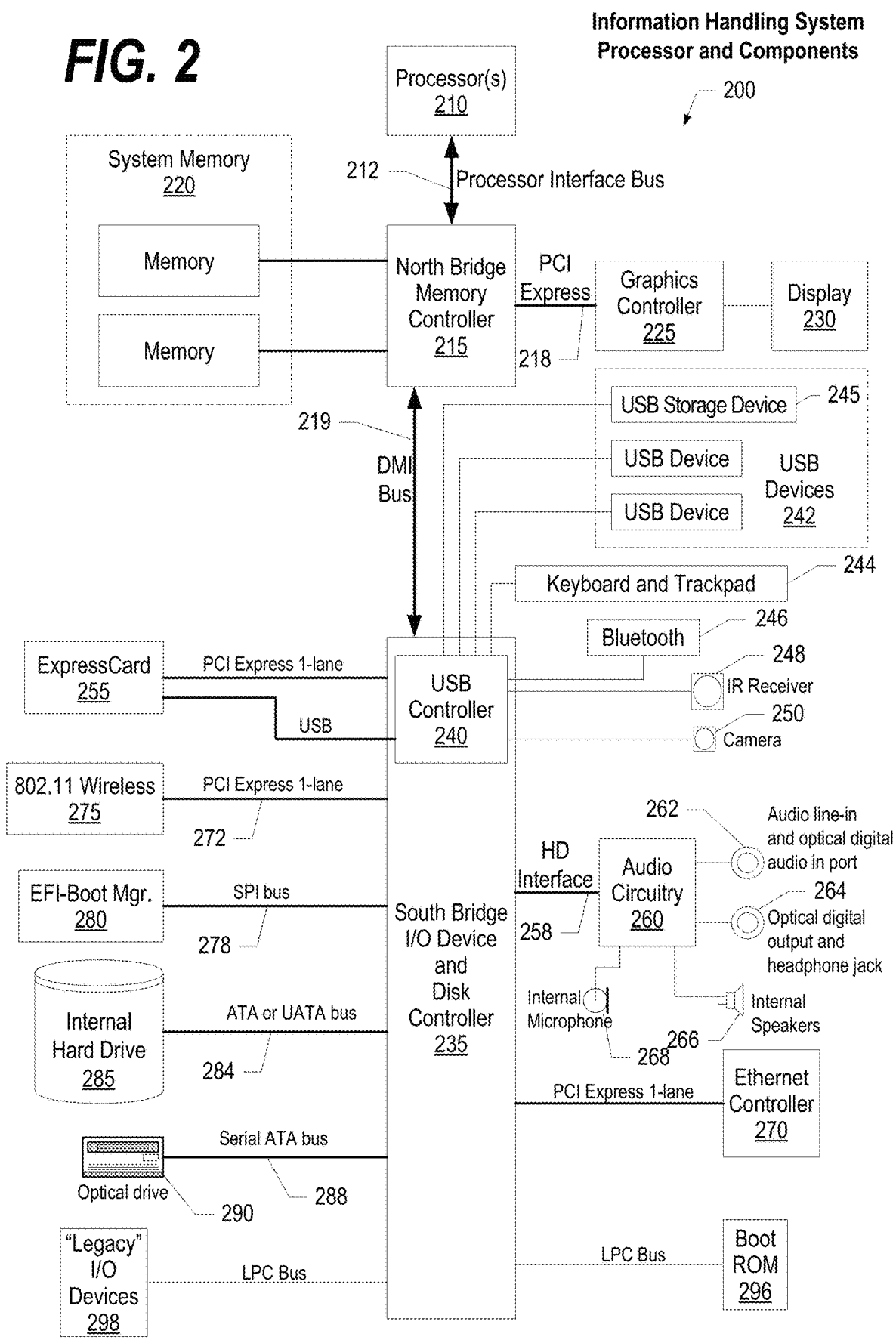
FIG. 2 illustrates an information handling system, more particularly, a processor and common components, which is a simplified example of a computer system capable of performing the computing operations described herein.

FIG. 2 illustrates information handling system 200, more particularly, a processor and common components, which is a simplified example of a computer system capable of performing the computing operations described herein. Information handling system 200 includes one or more processors 210 coupled to processor interface bus 212. Processor interface bus 212 connects processors 210 to Northbridge 215, which is also known as the Memory Controller Hub (MCH). Northbridge 215 connects to system memory 220 and provides a means for processor(s) 210 to access the system memory. Graphics controller 225 also connects to Northbridge 215. In one embodiment, PCI Express bus 218 connects Northbridge 215 to graphics controller 225. Graphics controller 225 connects to display device 230, such as a computer monitor.

Northbridge 215 and Southbridge 235 connect to each other using bus 219. In one embodiment, the bus is a Direct Media Interface (DMI) bus that transfers data at high speeds in each direction between Northbridge 215 and Southbridge 235. In another embodiment, a Peripheral Component Interconnect (PCI) bus connects the Northbridge and the Southbridge. Southbridge 235, also known as the I/O Controller Hub (ICH) is a chip that generally implements capabilities that operate at slower speeds than the capabilities provided by the Northbridge. Southbridge 235 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 296 and "legacy" I/O devices (using a "super I/O" chip). The "legacy" I/O devices (298) can include, for example, serial and parallel ports, keyboard, mouse, and/or a floppy disk controller. The LPC bus also connects Southbridge 235 to Trusted Platform Module (TPM) 295. Other components often included in Southbridge 235 include a Direct Memory Access (DMA) controller, a Programmable Interrupt Controller (PIC), and a storage device controller, which connects Southbridge 235 to nonvolatile storage device 285, such as a hard disk drive, using bus 284.

ExpressCard 255 is a slot that connects hot-pluggable devices to the information handling system. ExpressCard 255 supports both PCI Express and USB connectivity as it connects to Southbridge 235 using both the Universal Serial Bus (USB) the PCI Express bus. Southbridge 235 includes USB Controller 240 that provides USB connectivity to devices that connect to the USB. These devices include webcam (camera) 250, infrared (IR) receiver 248, keyboard and trackpad 244, and Bluetooth device 246, which provides for wireless personal area networks (PANs). USB Controller 240 also provides USB connectivity to other miscellaneous USB connected devices 242, such as a mouse, removable nonvolatile storage device 245, modems, network cards, ISDN connectors, fax, printers, USB hubs, and many other types of USB connected devices. While removable nonvolatile storage device 245 is shown as a USB-connected device, removable nonvolatile storage device 245 could be connected using a different interface, such as a Firewire interface, etcetera.

Wireless Local Area Network (LAN) device 275 connects to Southbridge 235 via the PCI or PCI Express bus 272. LAN device 275 typically implements one of the IEEE.802.11 standards of over-the-air modulation techniques that all use the same protocol to wireless communicate between information handling system 200 and another computer system or device. Optical storage device 290 connects to Southbridge 235 using Serial ATA (SATA) bus 288. Serial ATA adapters and devices communicate over a high-speed serial link. The Serial ATA bus also connects Southbridge 235 to other forms of storage devices, such as hard disk drives. Audio circuitry 260, such as a sound card, connects to Southbridge 235 via bus 258. Audio circuitry 260 also provides functionality such as audio line-in and optical digital audio in port 262, optical digital output and headphone jack 264, internal speakers 266, and internal microphone 268. Ethernet controller 270 connects to Southbridge 235 using a bus, such as the PCI or PCI Express bus. Ethernet controller 270 connects information handling system 200 to a computer network, such as a Local Area Network (LAN), the Internet, and other public and private computer networks.

While FIG. 2 shows one information handling system, an information handling system may take many forms, some of which are shown in FIG. 1. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

Figure 3:
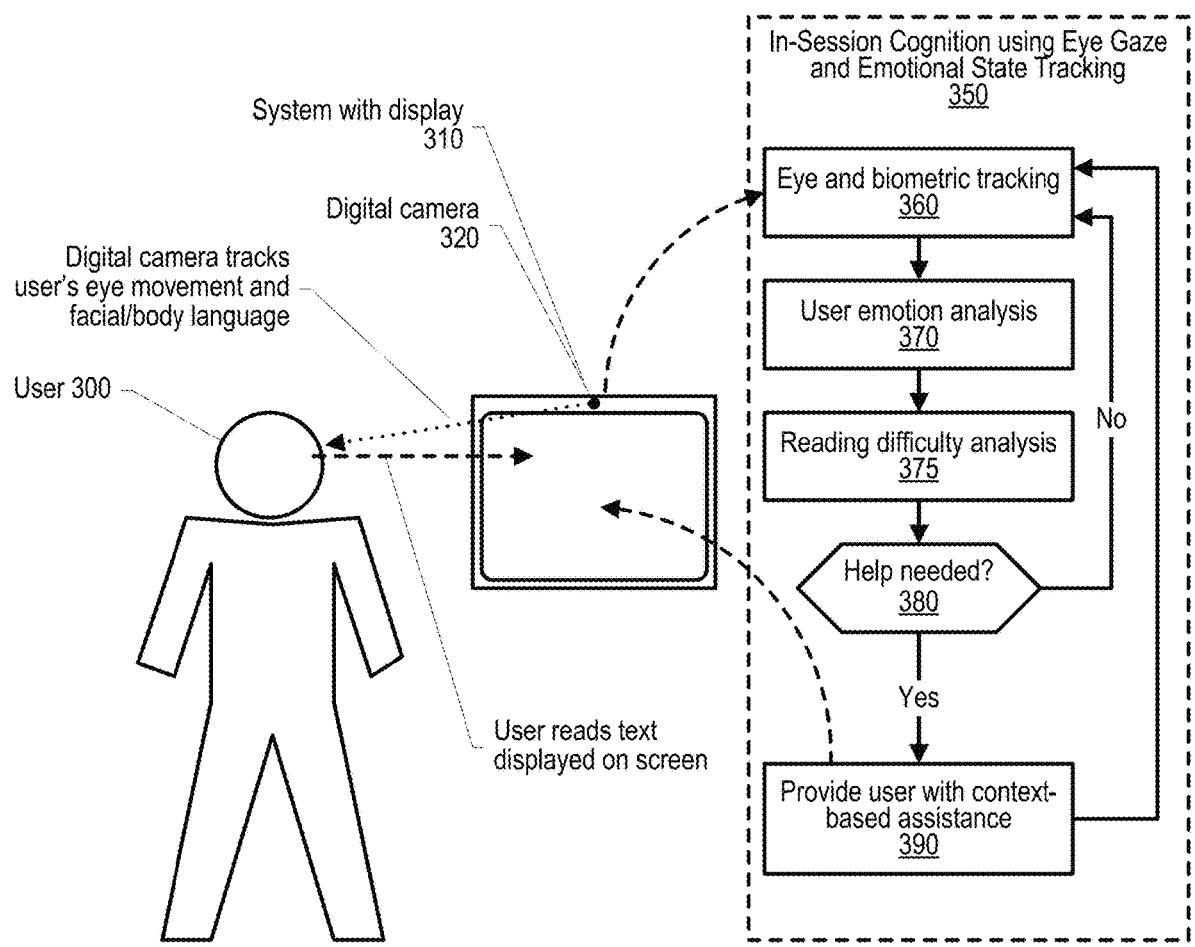
FIG. 3 is a system diagram depicting the components utilized to assist learners based on analytics of in-session cognition.

FIG. 3 is a system diagram depicting the components utilized to assist learners based on analytics of in-session cognition. User 300 is a reader of a document displayed on system with display 310. Like most any user, user 300 might require assistance when encountering unfamiliar terminology. The reasons for needing assistance are numerous and might include the user being a new reader, new to the subject area of the document, and a new speaker of the language in which the document is written. System with display 310 includes digital camera 320 that is used to track the user's eye movement as the user reads the document text displayed on the screen as well as to capture digital images of the user's facial expressions that are used to identify the user's current emotional state (e.g., confused, upset, relaxed, etc.). The eye movement tracking is used to detect which portion of the screen, and therefore document, is currently being read so that the system can identify any particular terms that the user might be reading and with which the user might be experiencing difficulty.

In-session cognition using eye gaze and emotional state tracking system 350 includes a number of base functions. Eye and biometric tracking 360 tracks the user's eye movement and gaze as the user reads document text displayed on screen 310. User emotion analysis 370 receives digital images captured of the user's facial expressions, analyzes these images, and determines the user's current emotional state which might indicate that the user is currently experiencing difficulty with terminology that the user is currently encountering in the document text. Reading difficulty analysis function 375 uses the user emotion analysis results coupled with the eye tracking data to identify terminology with which the user might be experiencing difficulty. A determination is made whether the analysis reveals that the user needs assistance with material currently being read (decision 380). If assistance is needed, then decision 380 branches to the 'yes' branch whereupon, at step 390, the system provides the user with non-obtrusive context-based assistance in the form of assistive texts. Processing loops back to continue tracking the user's eye movement and current emotional state in order to identify other terminology for which assistance might be needed.

In one embodiment, the assistance is provided non-obtrusively by creating hyperlinks of terms in the document that the analysis identified as possibly being difficult for the user to understand. In another embodiment, the identified terms in the document are presented outside the document text area (e.g., in the margin area, etc.) so that the user can "click" (select) a term of interest and receive the assistive text information corresponding to the selected term.

Further, in one embodiment, the assistive text information is gathered from other areas of the document furthering the probability that the user will be able to understand the assistive text with relation to the corresponding terminology. In another embodiment, where the user is reading a collection of documents, the assistive text information is gathered from such collection of documents so that the assistive text might be gathered from another document other than the document currently being read by the user. Finally, in one embodiment, other sources of information, such as online resources, can be used to gather the assistive text information, for example when the document and any collection of documents are not found to include assistive text corresponding to the particular terminology found in the document.

Figure 4:
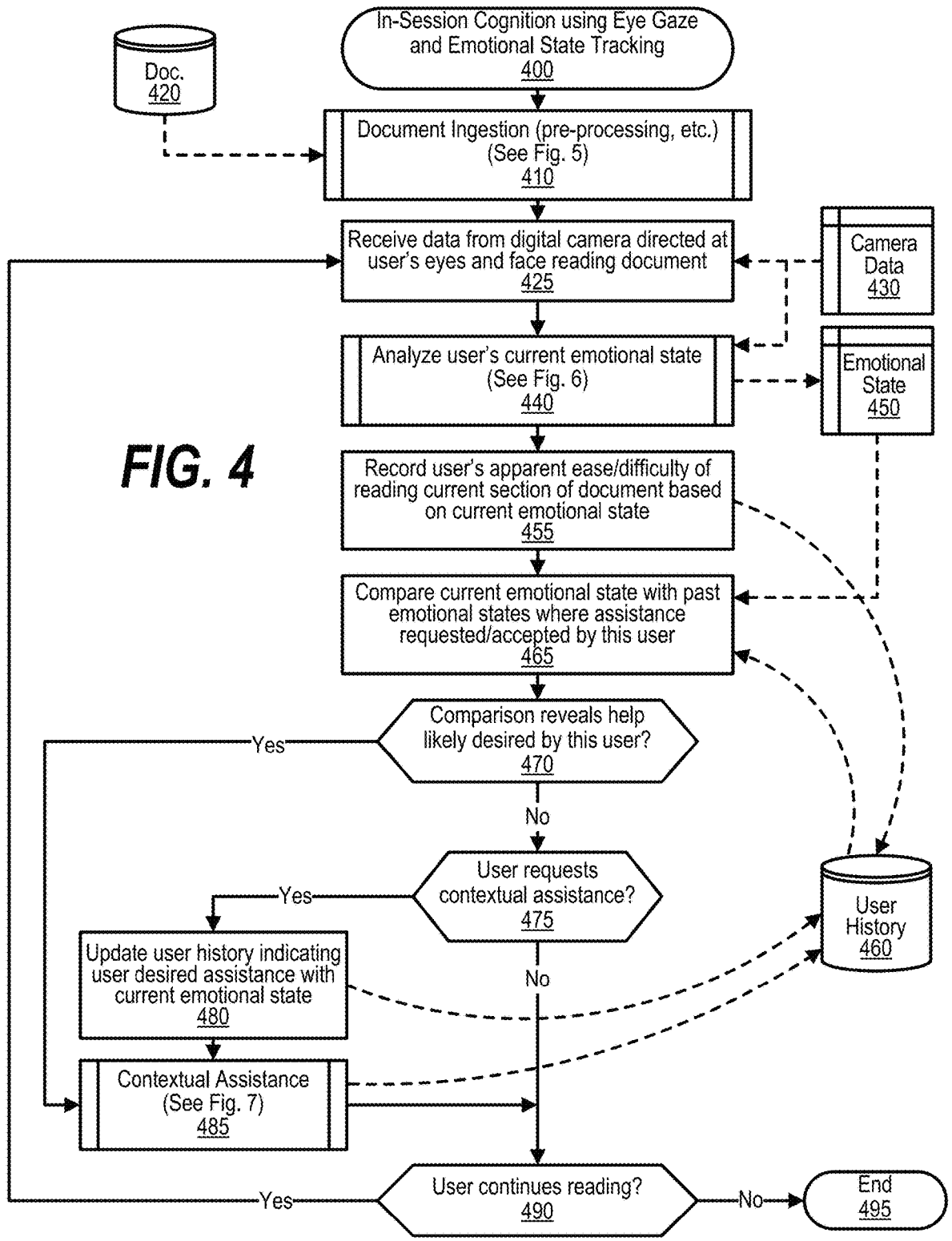
FIG. 4 is a flowchart showing steps performed by a routine that uses eye gaze and emotional state tracking for determining in-session cognition.

FIG. 4 is a flowchart showing steps performed by a routine that uses eye gaze and emotional state tracking for determining in-session cognition. FIG. 4 processing commences at 400 and shows the steps taken by a process that provides assistance using in-session cognition using eye gaze and emotional state tracking. At predefined process 410, the process performs the Document Ingestion routine (see FIG. 5 and corresponding text for processing details). This routine ingests document 420 displayed on the display screen by pre-processing the terminology found throughout the document. At step 425, the process receives data from a digital camera that is directed at the user's eyes and face while the user is reading the document on the screen. Camera data is received from memory area 430 after having been captured by the digital camera.

Figure 6:
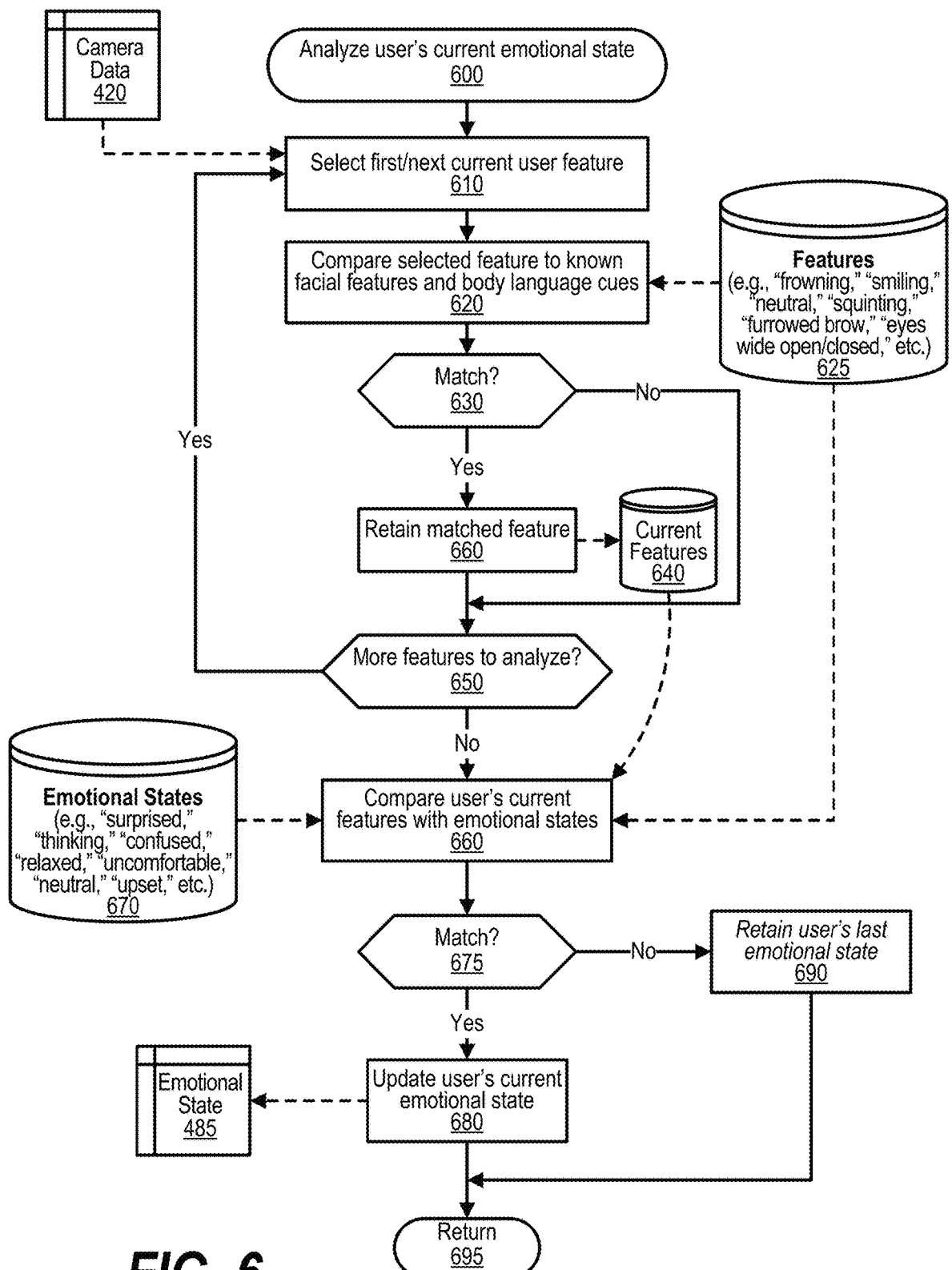
FIG. 6 is a flowchart showing steps performed by a routine that analyzes a user's current emotional state.

At predefined process 440, the process performs the Analyze User's Current Emotional State routine (see FIG. 6 and corresponding text for processing details). This routine uses digital images of the user's face captured by the digital camera to detect the user's current emotional state which is then stored in memory area 450. At step 455, the process records the user's apparent ease or difficulty found in the user's reading of the current section of the document based on the user's current emotional state. The user's difficulty in reading along with the terminology currently being read by the user are stored in the user's history data store 460.

At step 465, the process compares the user's current emotional state with past emotional states where the user requested or otherwise accepted reading assistance. The process determines as to whether the comparison performed at step 465 revealed that assistance is likely desired by the user (decision 470). If the comparison reveals that assistance is likely desired, then decision 470 branches to the 'yes' branch to perform predefined process 485 which provides contextual assistance. On the other hand, if the comparison does not reveal that assistance is needed, then decision 470 branches to the 'no' branch to continue processing. The process determines as to whether the user requested contextual assistance even though step 475 did not detect that assistance was currently needed (decision 475). If the user requests contextual assistance, then decision 475 branches to the 'yes' branch to perform steps 480 and predefined process 485. On the other hand, if the user does not request contextual assistance, then decision 475 branches to the 'no' branch bypassing step 480 and predefined process 485.

At step 480, the process updates the user history data stored in data store 460 indicating that the user requested assistance along with the user's current emotional state and the terminology with which the user experienced difficulty. At predefined process 485, the process performs the Contextual Assistance routine (see FIG. 7 and corresponding text for processing details). This routine provides the user with on-screen contextual assistance with terminology currently being viewed by the user on the display screen. The process determines as to whether the user continues reading the document or quits reading (decision 490).

If the user continues reading, then decision 490 branches to the 'yes' branch which loops back to step 425 to continue monitoring the user while reading the document and providing contextual assistance with terminology when difficulty detected. This looping continues until the user stops reading the document, at which point decision 490 branches to the 'no' branch exiting the loop and processing thereafter ends at 495.

Figure 5:
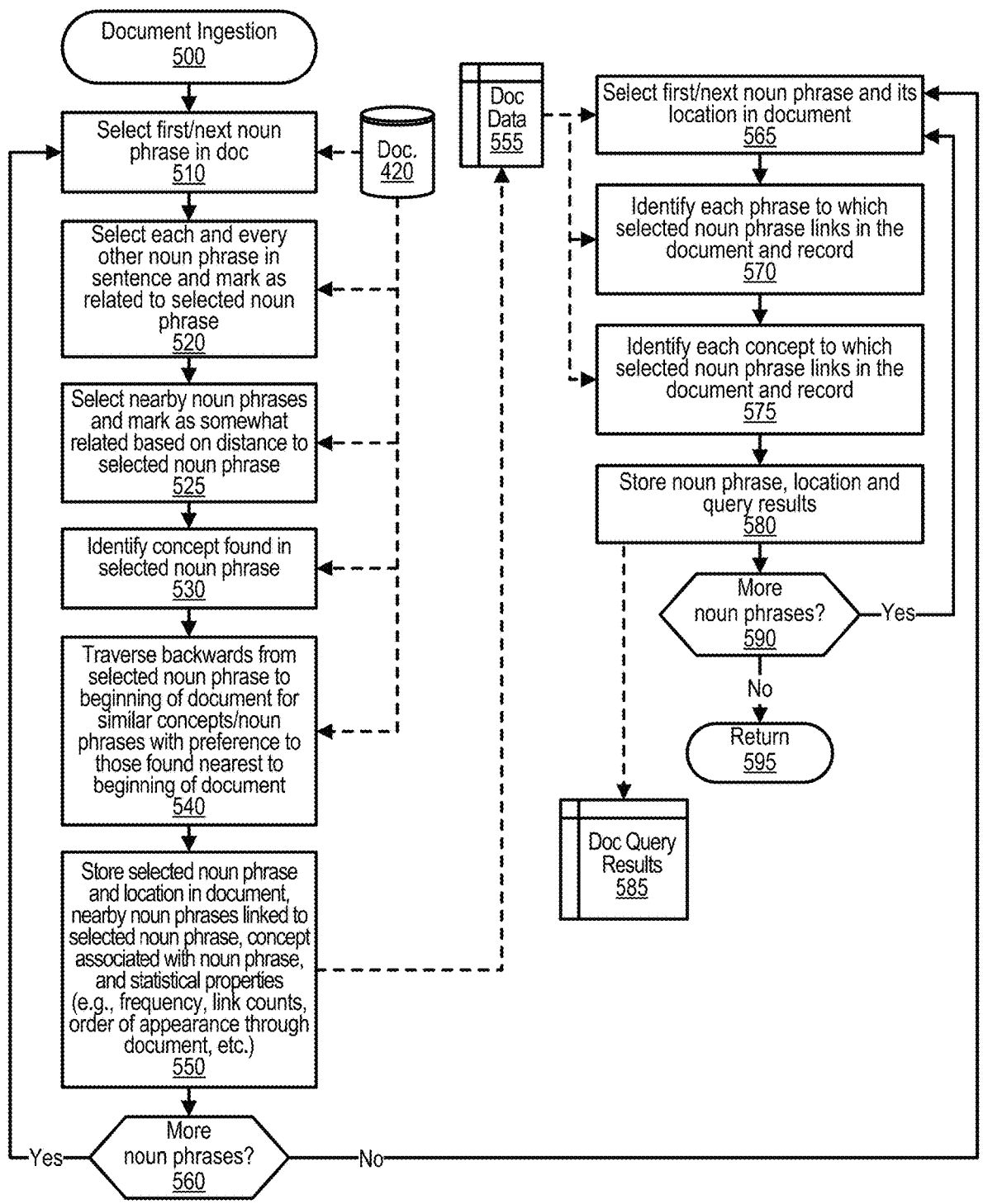
FIG. 5 is a flowchart showing steps performed by a document ingestion routine.

FIG. 5 is a flowchart showing steps performed by a document ingestion routine. FIG. 5 processing commences at 500 and shows the steps taken by a process that performs document Ingestion, such as on a document currently being read by the user. At step 510, the process selects the first terminology (e.g., noun phrase, etc.) found in document 420. At step 520, the process selects each and every other noun phrase in the sentence and marks these as being related to the selected noun phrase. At step 525, the process selects nearby noun phrases and mark these as being somewhat related to the selected terminology based on the distance between the selected terminology and the nearby noun phrases.

At step 530, the process identifies any concept found in the selected terminology (noun phrase). At step 540, the process traverses backwards from the selected terminology (noun phrase) to the beginning of the document for similar concepts and terminologies (e.g., noun phrases, etc.) with preference being given to those concepts and terminologies found nearest to the beginning of the document. At step 550, the process stores the selected terminology (noun phrase) and the terminology's location in the document along with nearby noun phrases that are linked to the selected terminology, concept associated with the terminology, and statistical properties (e.g., frequency, link counts, order of appearance through document, etc.) of the terminology. This data is stored in memory area 555.

The process determines as to whether there are more terms (e.g., noun phrases, etc.) in the document to ingest (decision 560). If there are more terms to ingest, then decision 560 branches to the 'yes' branch which loops back to step 510 to select and process the next term from document 420 as described above. This looping continues until there are no more terms to process, at which point decision 560 branches to the 'no' branch exiting the loop.

At step 565, the process selects the first terminology found in the document and its location in document with the term and location being retrieved from memory area 555. At step 570, the process identifies each phrase to which the selected terminology links to in the document and records this data in memory area 585. At step 575, the process identifies each concept to which the selected terminology links to in the document and records this data in memory area 585. At step 580, the process stores the selected terminology, its location, and the query results from steps 570 and 575 in query results memory area 585. The process next determines whether there are more terms from the document to process (decision 590). If there are more terms to process, then decision 590 branches to the 'yes' branch which loops back to step 565 to select the next terminology from memory area 555 and process the selected term as described above. This looping continues until all terms have been processed, at which point decision 590 branches to the 'no' branch exiting the loop. FIG. 5 processing thereafter returns to the calling routine (see FIG. 4) at 595.

FIG. 6 is a flowchart showing steps performed by a routine that analyzes a user's current emotional state. FIG. 6 processing commences at 600 and shows the steps taken by a process that analyzes the user's current emotional state. At step 610, the process selects the first current user feature from the digital image of the user's face that was captured and stored in memory area 420. At step 620, the process compares the selected feature to known facial features and body language cues. Known features are retrieved from data store 625 with examples of features being those showing the user "frowning," "smiling," "neutral," "squinting," "furrowed brow," "eyes wide open/closed," etc. The process determines as to whether the user's current facial features match any known features (decision 630). If they match, then decision 630 branches to the 'yes' branch to perform step 660. On the other hand, if they do not match, then decision 630 branches to the 'no' branch bypassing step 660.

At step 660, the process retains matched feature and stores it in data store 640. The process determines as to whether there are more features in the digital image yet to be analyzed (decision 650). If there are more features to analyze, then decision 650 branches to the 'yes' branch which loops back to step 610 to select and analyze the next feature from the digital image. This looping continues until there are no more features to analyze, at which point decision 650 branches to the 'no' branch exiting the loop. At step 660, the process compares the user's current features stored in data store 640 with known emotional states that are retrieved from data store 670. Known emotional states indicate which features indicate a particular emotion of the user. Examples of such emotional states include features that indicate that the user is "surprised," "thinking," "confused," "relaxed," "uncomfortable," "neutral," "upset," etc.

The process determines as to whether the user's current features match any of the known emotional states (decision 675). If they match, then decision 675 branches to the 'yes' branch whereupon, at step 680, the process updates the user's current emotional state and stores the current emotional state in memory area 485. On the other hand, if no match is found, then decision 675 branches to the 'no' branch whereupon, at step 690, the user's last known emotional state is maintained. FIG. 6 processing thereafter returns to the calling routine (see FIG. 4) at 695.

Figure 7:
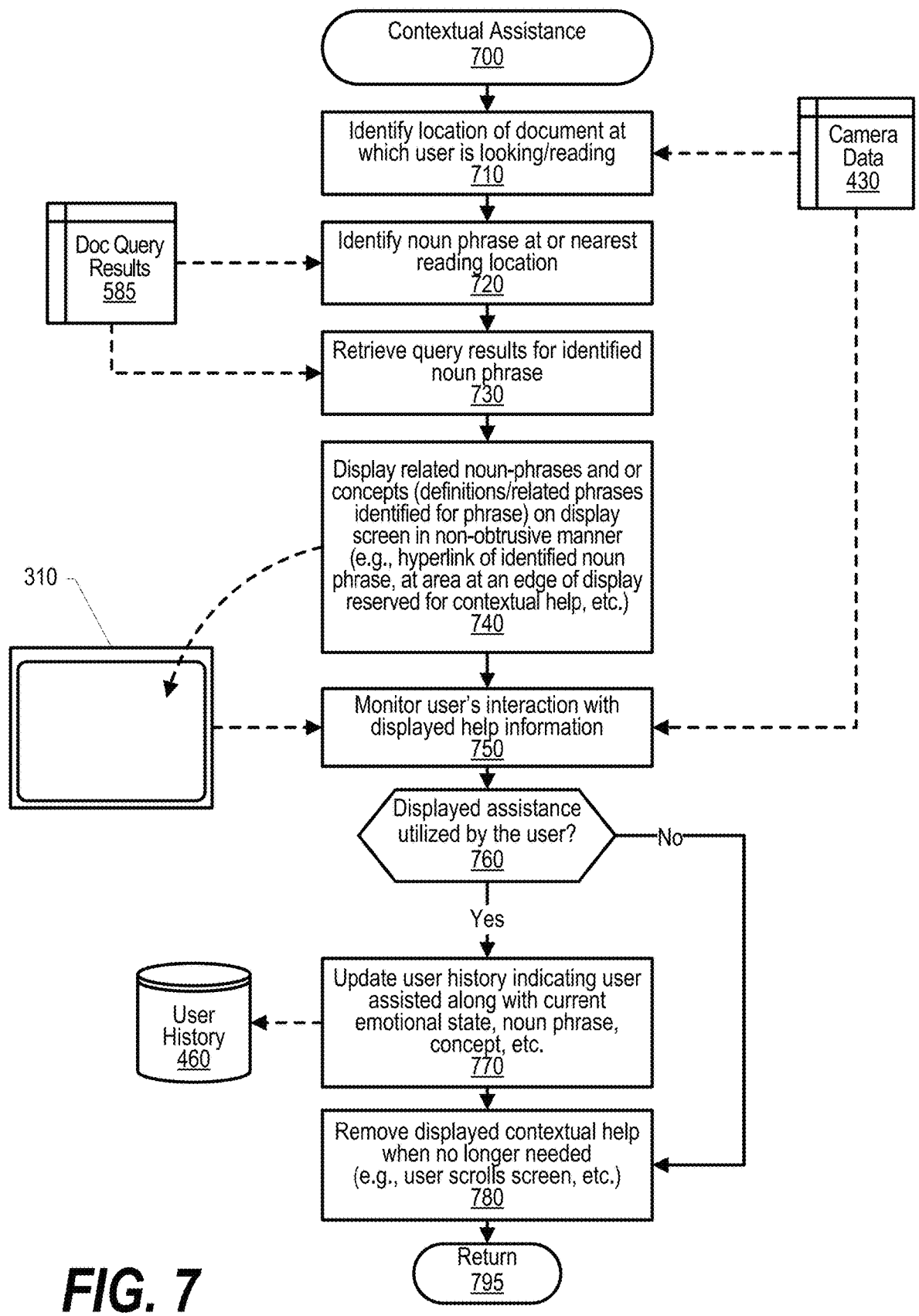
FIG. 7 is a flowchart showing steps performed by a routine that provides contextual assistance to a reader based on an understanding of the user's in-session cognition.

FIG. 7 is a flowchart showing steps performed by a routine that provides contextual assistance to a reader based on an understanding of the user's in-session cognition. FIG. 7 processing commences at 700 and shows the steps taken by a process that provides contextual assistance to the user. At step 710, the process identifies the location of the document at which user is currently reading by utilizing the eye gaze data retrieved from the digital camera data that is recording the user's eye movement. At step 720, the process next identifies any terminology (e.g., noun phrases, etc.) at or near the user's current reading location. At step 730, the process retrieves query results from memory area 585 corresponding to the identified terminology where the user is reading.

At step 740, the process displays the related noun-phrases and or concepts (definitions/related phrases identified for phrase, etc.) on display screen 310 in a non-obtrusive manner (e.g., hyperlink of identified noun phrase, at area at an edge of display reserved for contextual help, etc.). At step 750, the process monitors the user's interaction with the currently displayed assistance information. The process determines as to whether the displayed assistance information was utilized by the user (decision 760). If the displayed assistance was utilized by the user, then decision 760 branches to the 'yes' branch to perform step 770. On the other hand, if the displayed assistance was not utilized by the user, then decision 760 branches to the 'no' branch bypassing step 770.

At step 770, the process updates the user's history data stored in data store 460 indicating that the user was assisted along with the user's current emotional state, the terminology at issue, the concept of the terminology, etc. At step 780, the process removes displayed contextual assistance when such information is no longer needed by the user (e.g., user scrolls screen, eye gaze travels below the area on the screen, etc.). FIG. 7 processing thereafter returns to the calling routine (see FIG. 4) at 795.

While particular embodiments of the present invention have been shown and described, it will be obvious to those skilled in the art that, based upon the teachings herein, that changes and modifications may be made without departing from this invention and its broader aspects. Therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

The invention claimed is:

1. A method implemented by an information handling system comprising a processor and a memory accessible by the processor, the method comprising:
   ingesting a plurality of terms in a document;
   detecting, by a camera, a section of the document currently being read by a user on a display device, and one or more facial features of the user;
   determining, based on the one or more facial features, a current emotional state of the user;
   in response to determining, based on the current emotional state, that a reading assistance would be helpful to the user:
      identifying a terminology within the section of the document currently being read by the user;
      comparing the identified terminology with the ingested plurality of terms;
      retrieving one or more assistive texts related to the identified terminology, wherein the retrieving is based on the comparing, and wherein the retrieving comprises retrieving at least one of the assistive texts from one or more previous sections of the document; and
      displaying at least one of the assistive texts on the display device.

2. The method of claim 1 further comprising:
   displaying at least one non-obtrusive indicator on the display screen, wherein each of the non-obtrusive indicators corresponds to one of the assistive texts; and
   receiving, from the user, a request corresponding to a selected one of the non-obtrusive indicators, wherein a selected one of the assistive texts is responsively displayed, wherein the selected assistive text corresponds with the selected non-obtrusive indicator.

3. The method of claim 1 further comprising:
   detecting, using the camera, an eye gaze of the user that is directed to the display screen, wherein the section is detected based on a direction of the user's eye gaze.

4. The method of claim 1 further comprising:
   comparing the detected facial features to a set of known facial features, wherein the set of known facial features correspond to one or more emotional states, wherein the determined emotional state is based on the comparisons.

5. The method of claim 1 further comprising:
   retrieving at least one of the assistive texts from a previously accessed document, and at least one of the assistive texts from an online source.

6. An information handling system comprising:
   one or more processors;
   a memory coupled to at least one of the processors;
   a camera;
   a display device accessible by at least one of the processors; and
   a set of computer program instructions stored in the memory and executed by at least one of the processors in order to perform actions of:
      ingesting a plurality of terms in a document;
      detecting, by the camera, a section of the document currently being read by a user on the display device, and one or more facial features of the user;
      determining, based on the one or more facial features, a current emotional state of the user;
      in response to determining, based on the current emotional state, that a reading assistance would be helpful to the user:
         identifying a terminology within the section of the document currently being read by the user;
         comparing the identified terminology with the ingested plurality of terms;
         retrieving one or more assistive texts related to the identified terminology, wherein the retrieving is based on the comparing, and wherein the retrieving comprises retrieving at least one of the assistive texts from one or more previous sections of the document; and
         displaying at least one of the assistive texts on the display device.

7. The information handling system of claim 6 wherein the actions further comprise:
   displaying at least one non-obtrusive indicator on the display screen, wherein each of the non-obtrusive indicators corresponds to one of the assistive texts; and
   receiving, from the user, a request corresponding to a selected one of the non-obtrusive indicators, wherein a selected one of the assistive texts is responsively displayed, wherein the selected assistive text corresponds with the selected non-obtrusive indicator.

8. The information handling system of claim 6 wherein the actions further comprise:
   detecting, using a digital the camera, an eye gaze of the user that is directed to the display screen, wherein the section is detected based on a direction of the user's eye gaze.

9. The information handling system of claim 6 wherein the actions further comprise:
   comparing the detected facial features to a set of known facial features, wherein the set of known facial features correspond to one or more emotional states, wherein the determined emotional state is based on the comparisons.

10. The information handling system of claim 6 wherein the actions further comprise:
    retrieving at least one of the assistive texts from a previously accessed document, and at least one of the assistive texts from an online source.

11. A computer program product stored in a computer readable storage medium, comprising computer program code that, when executed by an information handling system, causes the information handling system to perform actions comprising:
    ingesting a plurality of terms in a document;
    detecting, by a camera, a section of the document currently being read by a user on a display device, and one or more facial features of the user;
    determining, based on the one or more facial features, a current emotional state of the user;

in response to determining, based on the current emotional state, that a reading assistance would be helpful to the user:
identifying a terminology within the section of the document currently being read by the user;
comparing the identified terminology with the ingested plurality of terms;
retrieving one or more assistive texts related to the identified terminology, wherein the retrieving is based on the comparing, and wherein the retrieving comprises retrieving at least one of the assistive texts from one or more previous sections of the document; and
displaying at least one of the assistive texts on the display device.

12. The computer program product of claim 11 wherein the actions further comprise:
displaying at least one non-obtrusive indicator on the display screen, wherein each of the non-obtrusive indicators corresponds to one of the assistive texts; and
receiving, from the user, a request corresponding to a selected one of the non-obtrusive indicators, wherein a selected one of the assistive texts is responsively displayed, wherein the selected assistive text corresponds with the selected non-obtrusive indicator.

13. The computer program product of claim 11 wherein the actions further comprise:
detecting, using the camera, an eye gaze of the user that is directed to the display screen, wherein the section is detected based on a direction of the user's eye gaze.

14. The computer program product of claim 11 wherein the actions further comprise:
comparing the detected facial features to a set of known facial features, wherein the set of known facial features correspond to one or more emotional states, wherein the determined emotional state is based on the comparisons.

* * * * *